(12) United States Patent
Wang

(10) Patent No.: US 9,719,900 B1
(45) Date of Patent: Aug. 1, 2017

(54) STRAIN-GAUGED WASHER FOR MEASURING BOLT PRELOAD

(71) Applicant: NORTHROP GRUMMAN SYSTEMS CORPORATION, Falls Church, VA (US)

(72) Inventor: Ge Wang, Los Alamitos, CA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 0 days.

(21) Appl. No.: 15/139,147

(22) Filed: Apr. 26, 2016

(51) Int. Cl.
*G01N 3/08* (2006.01)

(52) U.S. Cl.
CPC .................................... *G01N 3/08* (2013.01)

(58) Field of Classification Search
CPC ........................................................ G01N 3/08
USPC ............................... 73/818, 862.68, 862.625
See application file for complete search history.

(56) References Cited

U.S. PATENT DOCUMENTS

| | | | |
|---|---|---|---|
| 2,873,341 A | | 2/1959 | Kutsay |
| 2,998,585 A | * | 8/1961 | Bodner ................. F16B 31/028 338/5 |
| 3,151,258 A | | 9/1964 | Sonderegger et al. |
| 3,199,057 A | | 8/1965 | Gindes et al. |
| 3,237,507 A | | 3/1966 | Modrey |
| 3,285,120 A | | 11/1966 | Kartiala |
| 3,358,257 A | | 12/1967 | Painter et al. |
| 3,461,715 A | | 8/1969 | Stover, III |
| 3,826,131 A | | 7/1974 | Pritschow |
| 3,886,840 A | | 6/1975 | Bossler |
| 3,915,015 A | | 10/1975 | Crane et al. |
| 4,079,624 A | * | 3/1978 | Kurtz .................... G01L 1/2218 73/781 |
| 4,738,146 A | | 4/1988 | Baumgartner et al. |
| 4,770,049 A | | 9/1988 | Jones et al. |
| 4,889,457 A | * | 12/1989 | Hageman .............. F16B 31/028 411/10 |

(Continued)

FOREIGN PATENT DOCUMENTS

| | | | | |
|---|---|---|---|---|
| DE | 33 33 285 A1 | | 4/1985 | |
| DE | 3333285 A1 | * | 4/1985 | ............ F16B 31/028 |

(Continued)

OTHER PUBLICATIONS

Johnson, Eric C. et al. "Ultrasonic Method for Deployment Mechanism Bolt Element Preload Verification" Proceedings of the 42nd Aerospace Mechanisms Symposium, NASA Goddard Space Flight Center, May 14-16, 2014.

(Continued)

*Primary Examiner* — Lisa Caputo
*Assistant Examiner* — Jamel Williams
(74) *Attorney, Agent, or Firm* — John A. Miller; Miller IP Group, PLC

(57) ABSTRACT

This invention installs multiple miniature strain gauges inside a regular dimensioned bolt washer to accurately measure bolt preload. To enhance the strain gauge sensitivity, an alloy with low elastic modulus and high yield strength is selected to fabricate the metal washer. In addition, multiple gauges are connected in series to multiply the effective gauge length and enhance measurement sensitivity. Further, the stain gauges are encapsulated in the middle of the washer as opposed to on the external surface which offers much improved sensitivity and physical protection of the strain gauges.

19 Claims, 2 Drawing Sheets

(56) References Cited

U.S. PATENT DOCUMENTS

| | | | |
|---|---|---|---|
| 5,222,399 A * | 6/1993 | Kropp | F16B 31/028 |
| | | | 177/210 R |
| 5,361,642 A | 11/1994 | Welch | |
| 5,385,054 A * | 1/1995 | Kramer | F16B 31/028 |
| | | | 411/10 |
| 5,942,697 A | 8/1999 | Hesthamar et al. | |
| 6,250,863 B1 * | 6/2001 | Kamentser | F16B 31/028 |
| | | | 116/212 |
| 6,378,384 B1 | 4/2002 | Atkinson et al. | |
| 6,467,361 B2 * | 10/2002 | Rainey | G01L 1/2206 |
| | | | 73/862.637 |
| 6,792,815 B2 * | 9/2004 | McDearmon | G01L 5/161 |
| | | | 73/862.041 |
| 7,156,595 B2 * | 1/2007 | Clarke | G01L 5/243 |
| | | | 411/10 |
| 9,329,579 B2 * | 5/2016 | Slupsky | G01D 9/005 |
| 9,429,485 B1 * | 8/2016 | Cavallaro | G01L 1/04 |
| 2007/0193361 A1 | 8/2007 | Coffey et al. | |
| 2008/0006450 A1 | 1/2008 | Simons | |
| 2010/0208940 A1 * | 8/2010 | Takman | F16B 31/02 |
| | | | 382/103 |
| 2012/0073104 A1 | 3/2012 | Laursen et al. | |
| 2015/0128725 A1 | 5/2015 | Ichige et al. | |

FOREIGN PATENT DOCUMENTS

| | | | |
|---|---|---|---|
| EP | 0520380 A1 * | 12/1992 | F16J 15/064 |
| EP | 0 766 077 B1 | 12/2003 | |
| GB | 1 255 042 A | 11/1971 | |
| GB | 2 310 288 A | 8/1997 | |
| JP | S55-112540 A | 8/1980 | |
| JP | WO 2013172191 A1 * | 11/2013 | G01L 1/2231 |

OTHER PUBLICATIONS

Brown, Kevin H. et al. "Guideline for Bolted Joint Design and Analysis: Version 1.0" Sandia National Laboratories, Albuquerque, New Mexico and Livermore California, Sandia Report, SAND2008-03.71, Jan. 2008, pp. 1-46.

Li, Qing, et al. "Measurement and Control for Mechanical Compressive Stress" Sensors and Controls for Intelligent Manufacturing II, Proceedings of SPIE, vol. 4563, 2001, pp. 123-129.

* cited by examiner

US 9,719,900 B1

STRAIN-GAUGED WASHER FOR MEASURING BOLT PRELOAD

BACKGROUND

Field

This invention relates generally to a strain-gauged washer and, more particularly, to a conventional-thickness washer for measuring bolt preload including one or more strain gauges placed in a slot in the washer and oriented through a thickness of the washer to measure compressive strain in the washer, where the slot is located between an inner diameter and an outer diameter of the washer in order for the strain gauge to detect a maximum strain field, and more than one strain gauge may be connected in series in order to increase effective strain gauge length.

Discussion

Bolts are commonly used to fasten components together in assemblies of all types—ranging from simple, inexpensive household items to multi-billion dollar aircraft and space vehicles. Most bolted joints include a washer under the bolt head—where the washer serves to provide uniform contact and prevent damage to the underlying component.

In many bolted joint applications, it is important to achieve a prescribed preload in the bolt. Proper bolt preloading is effective in minimizing joint fatigue due to cyclic loading, and is also effective in preventing bolt loosening or back-out. Bolt preloading requirements are especially important in applications where the article of manufacture is large (requiring significant disassembly in order to access and replace/tighten a bolt), expensive (costly downtime for bolt replacement/tightening) and/or remotely deployed (impossible to replace/tighten a bolt on a satellite in space).

Many techniques for determining bolt preload have been developed over the years. One of the most basic forms of bolt preload estimation is through simple torque measurement during bolt tightening. However, surface friction and thread friction variations make torque-based bolt preload estimation inherently imprecise—with accuracies often no better than +/−30%. Other bolt preload techniques involve instrumentation or inspection of the bolt itself. These techniques also have disadvantages, however, including the cost and complexity of fitting sensors inside of the bolt, and the time and labor involved in performing ultrasound or other inspections on every bolt after it is installed. Still other bolt preload techniques involve the use of a thick collar in place of a standard washer under the bolt head, where the collar is fitted with instruments for measuring or estimating the load applied by the bolt head. However, these thick instrumented collars change the geometry of the bolted joint, necessitating a different bolt length to be used and/or dimensional changes to the fastened components.

As discussed above, all of the traditional techniques for bolt preload estimation or measurement suffer from significant drawbacks. Therefore, a need remains for a bolt preload measurement technique which is simple, inexpensive, reliable, accurate, and does not require any changes to the bolts or fastened components which are used in a bolted assembly.

DETAILED DESCRIPTION OF THE EMBODIMENTS

The following discussion of the embodiments of the invention directed to a strain-gauged washer for measuring bolt preload is merely exemplary in nature, and is in no way intended to limit the invention or its applications or uses. For example, the embodiments discussed below are described in the context of a flat washer employed between a flat bolt head and a flat fastened component. However, the disclosed invention is equally suitable for use in other shapes and configurations of washers and joint geometries.

Figure 1:
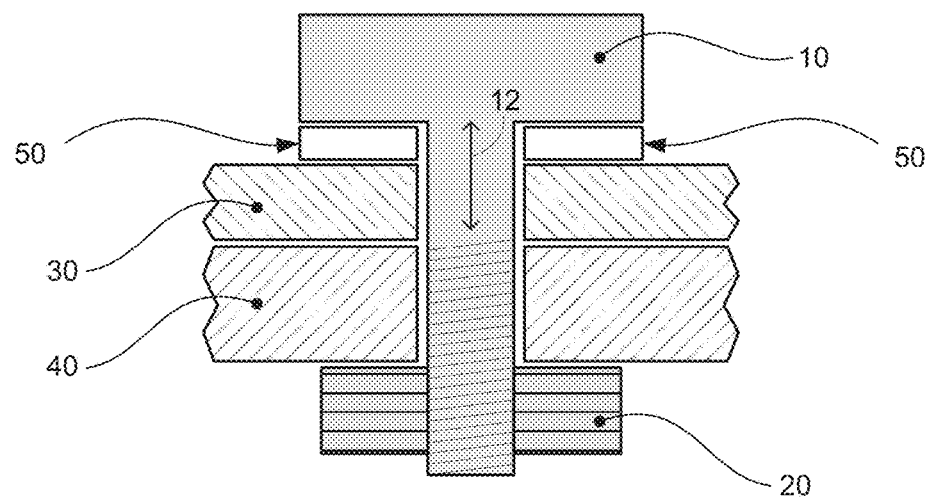
FIG. 1 is a cross-sectional illustration of a bolt and washer in a bolted-joint assembly.

FIG. 1 is a cross-sectional illustration of a bolted-joint assembly including a bolt 10, a nut 20, a first fastened component 30 and a second fastened component 40. To join the assembly, the bolt 10 is inserted through holes in the components 30 and 40, the nut 20 is threaded onto the extended end of the bolt 10, and the bolt 10 and the nut 20 are tightened. Alternatively, in lieu of the nut 20, the fastened component 40 may include a threaded portion into which the bolt 10 is threaded. A washer 50 is also included in the assembly, between the head of the bolt 10 and the adjacent surface of the first fastened component 30, as is commonly done and would be understood by anyone familiar with mechanical assemblies. Another washer (not shown) may also be used between the second fastened component 40 and the nut 20, where this additional washer may be a plain flat washer or lock washer, or it may be a strain-gauged washer according to the embodiments discussed below.

The bolt 10 has an axial direction 12, as shown in FIG. 1. The axial direction 12 is aligned along the length of the bolt 10; for example the axial direction 12 may be defined by the centerline of the bolt 10, where the bolt 10 is in tension in the axial direction 12 when the nut 20 is tightened to compress the assembly together.

Bolted joints are widely used in spacecraft construction and other long durability crafts and structures. To prevent joints from gapping and slipping, an adequate knowledge of the bolt preload is usually required in these applications. Often, such knowledge is gained by extensive structural testing of bolted joints and specification control of the bolt torque using a calibrated torque wrench. Also, in spacecraft and launch vehicle construction, mechanical separation devices rely on correct bolt preload for firing the separation device. In some cases, for example, separation bolts are made of shape memory alloys (SMA), and the separation load is linearly added to the bolt preload. Therefore, accurately measuring and controlling bolt preload is critically important in operation of SMA and similar separation devices.

Controlling bolt preload by specifying bolt tightening torque, preload estimation can be managed only to a precision of approximately 30%, due to variations in friction. On the other hand, direct measurement of bolt preload can allow this precision to be within a single digit. However, prior art techniques for measuring or estimating bolt preload have proven unsatisfactory for a variety of reasons. For example, measuring bolt elongation using ultrasonic waves offers improved preload precision over torque-based methods, but is labor intensive and not possible in some applications. Measuring bolt elongation using a strain gauge can also offer improved preload precision, but requires modification of the expensive and complex-shaped bolt. Installing thick collar-type measurement devices under the bolt head allows compressive load measurement, but changes the geometry of the bolted joint, necessitating use of a different bolt and/or modification of the fastened components.

The current invention embeds strain gauge sensors inside a standard-size washer used as part of the bolted joint. The compressive load inside the washer directly reflects the preload in the bolt. This device can be used with regular bolts without modification of either the bolt or the structural components which are being fastened by the bolt.

In the following discussions, a standard-sized washer is used as an example for illustration of the inventive concept. Specifically, a NAS1587 washer is illustrated—in both flat and countersunk varieties. NAS1587 is a family of washers designed to accommodate bolts ranging in size from ¼" diameter to 1¼" diameter, where all of the washers in the family have a thickness of 0.062" (or about 1.6 mm thickness). In one embodiment illustrated in the figures, a NAS1587-6C washer is shown, which is designed for a ⅜" bolt, has an inside diameter of about 0.38" and an outside diameter of about 0.69" and a conically-shaped inside diameter to accommodate a countersunk bolt head. For those skilled in the art, the concept explained below can be readily applied to other washers.

Embedding a strain sensor inside a washer rather than inside a bolt has not been done in the past due to the challenges involved. Specifically, the challenge of fitting a strain gauge with suitable sensitivity (accuracy) within the thickness of a standard-size washer. The gauge factor, or sensitivity, of a strain gauge is linearly proportional to the strain gauge length. These challenges are overcome by several aspects of this invention discussed below.

Firstly, modern strain gauge technology has advanced greatly to make small strain gauges possible. For example, strain gauges are now commercially available with gauge length as small as 0.2 mm, which is about an order of magnitude smaller than the thickness of the NAS1587 washer family discussed above.

Secondly, to enhance the strain gauge sensitivity for a short gauge length sensor, embodiments of the disclosed invention provide multiple strain gauges sensors embedded into the washer and connected in series, thus providing a longer effective gauge length. As such, the measured stain gauge resistance change is multiplied by the number of embedded strain sensors.

Thirdly, to further enhance the measurement sensitivity, materials are selected for fabrication of the washer which maximize the strain induced in the washer relative to bolt preload. By maximizing the compressive strain in the washer as a function of bolt preload (while of course ensuring that the washer material is strong enough to withstand the load), strain gauge sensitivity is improved.

Finally, modern finite element stress/strain analysis allows the strain field distribution inside a washer under a bolt load to be studied. This analysis provides the optimal locations for embedding strain gauge sensors inside a washer, further increasing the sensitivity and effectiveness of the strain gauges.

Figure 2:
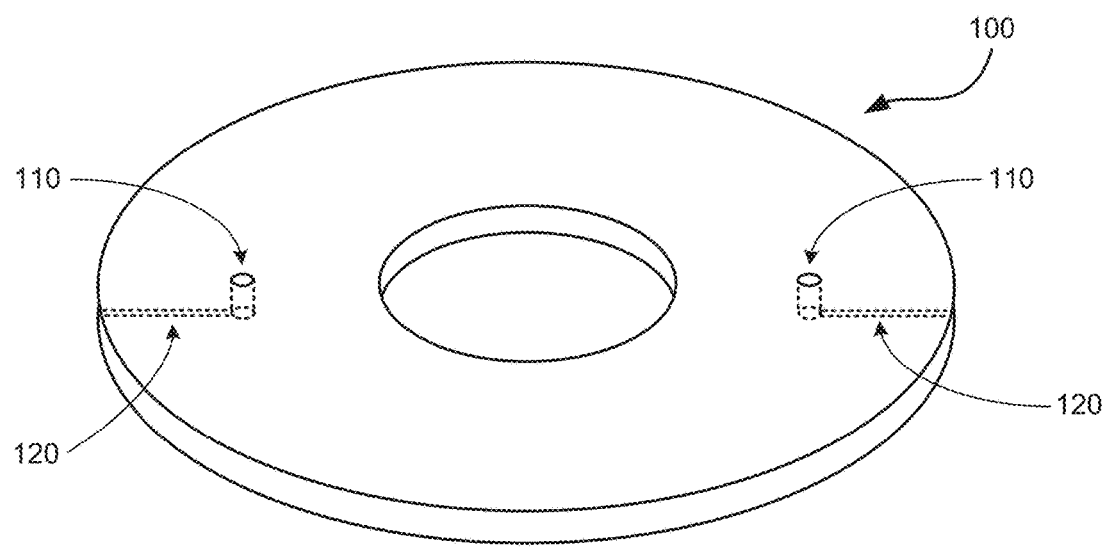
FIG. 2 is an isometric view illustration of a washer configured to include strain gauges oriented through the thickness of the washer to directly measure compressive strain.

FIG. 2 is an isometric view illustration of a washer 100 configured to directly measure compressive strain and therefore bolt preload in a bolted-joint assembly, according to a preferred embodiment of the invention. The washer 100 could be used as the washer 50 in the assembly of FIG. 1, as the washer 100 is a standard-sized flat washer such as, for example, one of the NAS1587 washers having a thickness of 1.6 mm discussed previously.

The washer 100 is configured with one or more small vertical slots 110. In the embodiment shown in FIG. 2, two of the slots 110 are provided, on opposite sides from each other surrounding the center bolt hole. The slots 110 are located about half-way between the inner diameter (ID) of the washer and the outer diameter (OD) as shown. The term "vertical" is used to describe the slots 110, where "vertical" means aligned with the axial direction 12 of the bolt 10, discussed previously. In a preferred embodiment, the slots 110 are round holes drilled or otherwise formed through the entire thickness of the washer 100. The washer 100 also includes a channel 120 extending from each of the slots 110 to the outer diameter of the washer 100. The channel(s) 120 allow for signal wires to be routed from the slot 110 to the outer diameter of the washer 100. FIG. 2 shows just the configuration of the washer 100 itself; additional details of the invention are discussed below.

Figure 3:
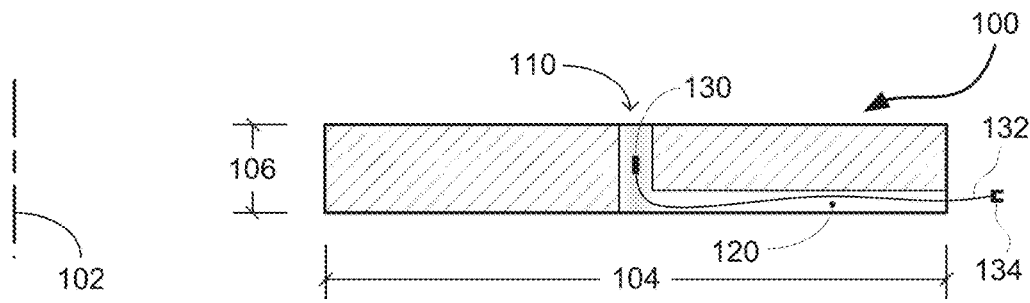
FIG. 3 is a cross-sectional illustration of a first configuration of strain-gauged washer according to an embodiment of the invention.

FIG. 3 is a cross-sectional illustration of the washer 100 of FIG. 2. FIG. 3 (along with FIGS. 4-5 discussed below) shows just one half of the cross-section of the washer 100—specifically, the right-hand half—as indicated by centerline 102 visible at the left. The opposite side of the washer 100 may be similarly configured—that is, a mirror image of what is shown in FIG. 3. Furthermore, the cross-section shown in FIG. 3 may be repeated multiple times around the circumferential direction of the washer 100—such as four of the slots 110 at equally-spaced 90° intervals. The same is true of FIGS. 4-5.

The half cross-section of the washer 100 has a width 104 and a thickness 106, which depend on exactly which washer size is used in a particular application. The width 104 is of course equal to one-half of the difference between the OD and the ID. The shape of the washer 100 shown in FIGS. 2 and 3 corresponds with one of the larger-diameter washers from the NAS1587 family, such as a 2" outer diameter washer, having the standard thickness (1.6 mm).

The slot 110 and the channel 120, shown in FIG. 2 and discussed above, are seen more clearly in the cross-sectional view of FIG. 3. The slot 110 may be a round hole drilled all the way through the thickness of the washer 100, as discussed above. The channel 120 may have any suitable cross-sectional shape (for example, U-shaped with rounded or square corners), and extends from the slot 110 to the outer peripheral edge of the washer 100.

A strain gauge 130 is attached to an inner surface of the slot 110. As discussed above, strain gauges are commercially available which are small enough to easily fit within the thickness 106 of the washer 100. The strain gauge 130 is oriented "vertically" in the slot 110—that is, parallel with the axial direction 12 of the bolt 10, so that the strain gauge 130 measures compressive strain in the washer 100. The strain gauge 130 may be attached to the inner surface of the slot 110 in any typical fashion, such as by bonding. The backing material on the strain gauge 130 may be trimmed in order to provide a proper fit within the slot 110.

If two of the slots 110 are provided in the washer 100, as shown in FIG. 2, then one of the strain gauges 130 is provided in each of the slots 110 and the two gauges 130 are wired in series and form gauge elements of a Wheatstone quarter bridge. The serial connection of the two gauges 130 multiplies as well as balances the strain gauge measurement as compared to a single strain gauge configuration.

An insulated wire 132 connects the strain gauge 130 to a connector 134, where the wire 132 passes though the channel 120 and extends to the exterior periphery of the washer 100. The connector 134 is preferably a miniature connector, for example, a micro USB connector, suitable for attachment to a data collection/display instrument (not shown). The wire 132 carries a data signal (a voltage) from the strain gauge 130 to the data collection instrument. The data collection instrument may be used to calibrate strain gauge readings to actual bolt preload in a controlled laboratory-type setting, and may be used to monitor strain gauge readings and display bolt preload in real time during actual production assembly of the bolted-joint.

The wires 132 may be encapsulated inside the channels 120 using a polymeric compound, for example, a polyurethane compound, or an epoxy. The encapsulation material is applied so as to have a height which does not protrude beyond the surface of the washer 100.

The washer 100 may be constructed using a standard stainless steel material. However, as an enhancement to the preferred embodiment, a titanium alloy, such as Ti-6Al-4V heat treated to STA condition, is used to make the washer 100. Titanium alloys have a very high yield strength, yet have an elastic modulus (stiffness) which is about 40% less than the modulus (stiffness) of the stainless steel which is typically used to make NAS washers. Thus, a titanium alloy washer can produce over one and a half times the elastic strain under the same load as compared to stainless steel. The increased strain magnitude of the washer 100 when composed of titanium further enhances the strain gauge sensitivity to bolt preload.

Figure 4:
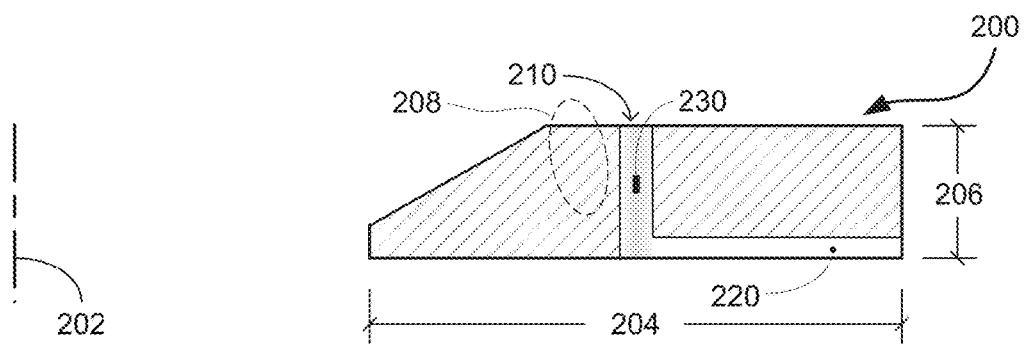
FIG. 4 is a cross-sectional illustration of a second configuration of strain-gauged washer according to an embodiment of the invention.

FIG. 4 is a cross-sectional illustration of a washer 200 which is a second configuration of strain-gauged washer according to an embodiment of the invention. The washer 200 of FIG. 4 has a shape which approximately corresponds to a NAS1587-6C washer, which has a width 204 of 0.155" (3.9 mm) and a thickness 206 of 0.062" (1.6 mm), and is shaped to accommodate a countersunk-style bolt head. The washer 200 includes (in the portion shown in FIG. 4; others may be included elsewhere in the washer 200) a slot 210, a channel 220 and a strain gauge 230, which are comparable to the corresponding items in FIG. 3. The signal wire leading from the strain gauge 230 through the channel 220 to an outer periphery of the washer 200 is not shown, for the sake of simplicity and clarity.

As mentioned earlier, finite element analysis (FEA) can be performed on a washer compressed under a bolt head to determine the strain field in the washer. Such a finite element analysis was performed on the washer 200, simulating a NAS1587-6C washer compressed from above by a flat-head bolt which extends to the outer diameter of the washer 200. (The washer 200, although designed to accommodate a countersunk-style bolt head, may also be used with flat-head bolts, for example where the bolt has a large-radius fillet blending the bolt shank to the bolt head, and the conical relief of the washer ID allows room for the fillet.)

The FEA of the washer 200 resulted in a strain field which was greatest in a region 208 depicted in FIG. 4. In order to optimize the sensitivity of the strain gauge 230, the slot 210 and the strain gauge 230 may be placed within or very near to the maximum strain region 208. Such a configuration results in maximum compression of the strain gauge 230 for a given bolt preload, thereby delivering optimum strain gauge sensitivity and bolt preload accuracy. The slot 210 in FIG. 2 is shown slightly displaced from the region 208 simply for clarity. If more than one of the slots 210 and the strain gauges 230 are used in the washer 200, they would preferably all be located at the same diameter, at spaced-apart positions around a circle. FEA of any bolt head and washer combination can readily be performed, where the results of the FEA will prescribe the location of maximum washer strain and hence the optimal location for slot and strain gauge placement.

Figure 5:
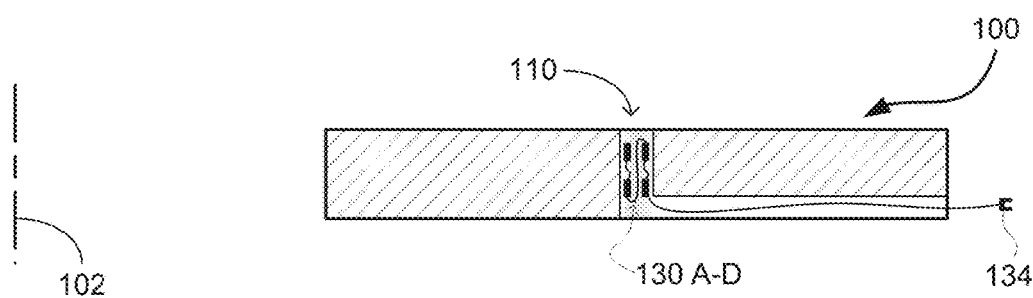
FIG. 5 is a cross-sectional illustration of a strain-gauged washer including a plurality of strain gauges in series within each slot in the washer, according to another embodiment of the invention.

FIG. 5 is a cross-sectional illustration of the strain-gauged washer 100 including a plurality of strain gauges 130 A-D within each of the slots 110 in the washer 100, according to another embodiment of the invention. In this embodiment, four of the strain gauges 130 A-D are arranged in the slot 110 and connected in series, thus providing an increased effective strain gauge length and increasing the sensitivity of the output signal. In this way, for a given bolt preload, the strain gauge output signal will be four times greater than it would be for a single strain gauge in the slot 110. More or fewer than four of the strain gauges 130 can be used in a single slot 110, with the main constraint simply being physical space within the slot 110. Multiple slots 110 can be employed in the washer 100, as shown in FIG. 2, with multiple strain gauges within each of the slots 110, as shown in FIG. 5, to provide a magnified and balanced signal proportional to bolt preload.

To those skilled the art, other implementations of the strain-gauged washer for bolt preload measurement can be readily realized in multiple ways. One example is to make the washer using other materials with low elastic modulus but high strength, in order to maximize the actual strain magnitude in the washer and thereby improve output signal strength. Several candidate alloys can be made of magnesium, zirconium, erbium, aluminum, hafnium, gold, silver, niobium, zinc, titanium, palladium, vanadium, copper or a combination thereof.

Another example is to place strain gauges in four equally-spaced slots around the face of the washer, thus making the system of strain gauges quadruple multiplied and balanced. Referring back to FIG. 2, four (or more) of the slots 110 can be included so that multiple strain gauges can be installed to further enhance the measurement sensitivity and balance out any off-axial moment of the bolt. Yet another embodiment includes multiple strain gauge sensors and temperature sensors into a single washer so that a full Wheatstone bridge and fully temperature compensated strain gauge washer is realized.

Still another example is to use strain gauges fabricated using microelectromechanical systems (MEMS) technologies in lieu of regular metal foil gauges. These MEMS devices can further miniaturize the sensors and permit installation on smaller washers, or the use of more strain gauges within a single slot.

The strain-gauged washer for measuring bolt preload described above provides numerous advantages over previous systems. These advantages include greatly improved strain gauge sensitivity compared to other systems—due to placement of the strain gauges within the interior of the washer to directly measure compressive strain in the maximum strain region of the washer, the use of multiple strain gauges connected in series to amplify the output signal, and the selection of a washer material which maximizes absolute strain while still elastically withstanding the compressive stress. Advantages of the disclosed invention also include the extremely low cost and small size of the strain-gauged washer, where the strain-gauged washer can be used in place of any standard-size washer in a bolted joint. This combination of features facilitates bolt preload measurement which is accurate, repeatable, inexpensive, and does not require changes to the bolt specifications or the design of the fastened assembly—thereby enabling bolt preload measurement to be reliably employed in any assembly where bolt preload criteria are important.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A strain-gauged washer for measuring a preload in a bolt, said washer comprising:
    a washer body having an inner diameter (ID) sized to fit around a shank of the bolt, an outer diameter (OD) based on a size of a head of the bolt, and a thickness which is standard for a flat washer with the ID and the OD, said washer body including one or more slots which are holes drilled completely through the thickness of the washer body and located between the ID and the OD of the washer body; and
    one or more strain gauges affixed within each of one or more slots in the washer body, where the strain gauges are oriented through the thickness of the washer body to detect compressive strain, and where the strain gauges provide an output signal corresponding to the preload in the bolt when the bolt is tightened.

2. The washer of claim 1 further comprising a signal wire leading from the strain gauges through a channel formed in a face of the washer body to an outer periphery of the washer body, said signal wire terminating in a connector, said signal wire carrying the output signal from the strain gauges.

3. The washer of claim 1 wherein the thickness of the washer body is less than 2 millimeters.

4. The washer of claim 1 wherein two or more strain gauges are affixed within each of the one or more slots in the washer body, and the strain gauges within each slot are connected in series in order to increase an effective strain gauge length and improve output signal sensitivity.

5. The washer of claim 1 wherein two or more strain gauges are affixed within a corresponding number of slots in the washer body, where one strain gauge is affixed within each slot, and where the slots are equally spaced in a circular pattern concentric with a center of the washer body.

6. The washer of claim 5 wherein the circular pattern has a diameter which is within 10 percent of an average of the OD and the ID.

7. The washer of claim 5 wherein four of the slots are located at 90° position intervals around the washer body, with one of the strain gauges affixed in each of the slots, and the strain gauges are connected to create a full Wheatstone bridge circuit.

8. The washer of claim 1 further comprising temperature sensors in one or more of the slots, where signals from the temperature sensors are used for temperature compensation of the output signal from the strain gauges to enable bolt preload measurement calibration over a range of temperatures.

9. The washer of claim 1 wherein the washer body is composed of a material having a minimal elastic modulus while also having a yield strength high enough to elastically withstand a stress induced by the bolt preload.

10. The washer of claim 1 wherein the washer body is composed of a Ti-6Al-4V titanium alloy heat treated to STA condition.

11. The washer of claim 1 wherein the strain gauges are fabricated using microelectromechanical systems (MEMS) technology.

12. The washer of claim 1 wherein the washer body has a countersunk-style shape including a conical chamfer from the ID to an upper face of the washer body, and the one or more slots are located between the conical chamfer and the OD.

13. A strain-gauged washer for measuring a preload in a bolt, said washer comprising:
    a washer body having an inner diameter (ID), an outer diameter (OD), and a thickness which are selected from a family of washers having a NAS1587 specification, said washer body including two or more slots which are holes drilled completely through the thickness of the washer body, where the slots are equally spaced in a circular pattern concentric with and located between the ID and the OD of the washer body; and
    at least one strain gauge affixed within each of the two or more slots in the washer body, where the strain gauges are oriented through the thickness of the washer body to detect compressive strain, and where the strain gauges provide an output signal corresponding to the preload in the bolt when the bolt is tightened.

14. The washer of claim 13 further comprising a signal wire leading from each of the slots through channels formed in a face of the washer body to an outer periphery of the washer body, said signal wire terminating in a connector, said signal wire carrying the output signal from the strain gauges.

15. The washer of claim 13 wherein four of the slots are located at 90° position intervals around the washer body, where the strain gauges are connected to create a full Wheatstone bridge circuit.

16. The washer of claim 13 wherein two or more strain gauges are affixed within each of the slots in the washer body, where the strain gauges in each of the slots are connected in series in order to increase an effective strain gauge length and improve output signal sensitivity.

17. The washer of claim 13 wherein the washer body is composed of a Ti-6Al-4V titanium alloy heat treated to STA condition.

18. A system for measuring a preload in a bolt, said system comprising:
    a strain-gauged washer including a washer body having an inner diameter (ID) sized to fit around a shank of the bolt, an outer diameter (OD) based on a size of a head of the bolt, and a thickness which is standard for a flat washer with the ID and the OD, and two or more strain gauges affixed within one or more holes formed completely through the thickness of the washer body, where the strain gauges are oriented through the thickness of the washer body to detect compressive strain, the holes are located between the ID and the OD of the washer body in order for the strain gauges to detect a maximum strain field in the washer body, and the strain gauges are connected in series in order to increase an effective strain gauge length and improve output signal sensitivity, and where the strain gauges provide an output signal corresponding to the preload in the bolt when the bolt is tightened;
    a signal wire leading from each of the strain gauges through channels formed in a face of the washer body to an outer periphery of the washer body, said signal wire terminating in a connector, said signal wire carrying the output signal from the strain gauges; and a measurement instrument attached to the connector and receiving the output signal, where the instrument displays the preload in the bolt in real time as the bolt is tightened.

19. The system of claim 18 further comprising a temperature sensor in one or more of the holes, where signals from the temperature sensor are received by the measurement instrument and used for temperature compensation of the output signal from the strain gauges.

\* \* \* \* \*